(12) United States Patent
Bonk et al.

(10) Patent No.: US 6,391,405 B1
(45) Date of Patent: *May 21, 2002

(54) FLUID BARRIER MEMBRANES

(75) Inventors: Henry W. Bonk, Wallingford, CT (US); David J. Goldwasser, Hillsboro; Paul H. Mitchell, Portland, both of OR (US)

(73) Assignee: Nike, Inc., Beaverton, OR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/211,093

(22) Filed: Dec. 14, 1998

Related U.S. Application Data

(63) Continuation-in-part of application No. 08/571,160, filed on Dec. 12, 1995, now Pat. No. 6,013,340, which is a continuation-in-part of application No. 08/475,275, filed on Jun. 7, 1995, now abandoned.

(51) Int. Cl.⁷ .................. B32B 27/40; A47C 16/00; A43B 13/00; A43B 21/00
(52) U.S. Cl. .............. 428/35.2; 428/35.5; 428/35.7; 428/36.8; 428/423.1; 5/655.3; 36/29; 36/35 B
(58) Field of Search ............... 428/35.2, 35.5, 428/35.7, 36.8, 423.1; 36/28, 29, 35 R, 35 B; 5/706, 707, 655.3; 138/30; 297/452.48; 152/157, 155, 246, 450

(56) References Cited

U.S. PATENT DOCUMENTS

| 3,718,494 A | 2/1973 | Jacobson |
| 4,082,854 A | 4/1978 | Yamada et al. |
| 4,257,176 A | 3/1981 | Hartung et al. |
| 4,340,626 A | 7/1982 | Rudy |
| 4,344,987 A | 8/1982 | Ostertag et al. |
| 4,423,185 A | 12/1983 | Matsimoto et al. |
| 4,429,076 A | 1/1984 | Saito et al. |
| 4,501,790 A | 2/1985 | Aizawa et al. |

(List continued on next page.)

FOREIGN PATENT DOCUMENTS

| EP | 624463 | 11/1994 |
| FR | 2636638 | 3/1990 |
| JP | 52-069486 | 6/1977 |
| JP | 58-22163 | 2/1983 |
| JP | 59-196706 | 11/1984 |
| JP | 59-116145 | 5/1987 |
| JP | 62-253428 | 11/1987 |
| WO | WO 8705563 | 9/1987 |

OTHER PUBLICATIONS

Bayer Polymers Division, Engineering Polymers Properties Guide, Thermoplastics and Thermosets.

*Primary Examiner*—Rena L. Dye
(74) *Attorney, Agent, or Firm*—Harness, Dickey & Pierce P.L.C.

(57) ABSTRACT

The invention provides amembrane that includes as a gas-barrier component a polyester polyol-modified polyurethane, the polyester polyol portion having repeating units in which the total number of carbon atoms is about eight or less. The membrane has a gas transmission rate of 15.0 or less for nitrogen gas.

20 Claims, 8 Drawing Sheets

U.S. PATENT DOCUMENTS

| | | | |
|---|---|---|---|
| 4,513,058 A | 4/1985 | Martin | |
| 4,536,425 A | 8/1985 | Hekal | |
| 4,551,518 A | 11/1985 | Matsiumoto et al. | |
| 4,557,859 A | 12/1985 | Maeda et al. | |
| 4,610,099 A | 9/1986 | Signori | |
| 4,614,208 A | 9/1986 | Skarelius | |
| 4,639,471 A | 1/1987 | Hirai et al. | |
| 4,681,797 A | 7/1987 | Van Iseghem | |
| 4,692,361 A | 9/1987 | Johnston et al. | |
| 4,722,131 A | 2/1988 | Huang | |
| 4,731,289 A * | 3/1988 | Coleman | 428/334 |
| 4,786,685 A | 11/1988 | Takida et al. | |
| 4,864,738 A | 9/1989 | Horovitz | |
| 4,874,670 A | 10/1989 | Boon et al. | |
| 4,887,367 A | 12/1989 | Mackness et al. | |
| 4,890,822 A | 1/1990 | Ezure et al. | |
| 4,927,689 A | 5/1990 | Markiewicz | |
| 4,936,029 A | 6/1990 | Rudy | |
| 4,960,639 A | 10/1990 | Oda et al. | |
| 4,978,394 A | 12/1990 | Ostertag et al. | |
| 4,999,229 A | 3/1991 | Moritani et al. | |
| 5,003,002 A | 3/1991 | Ofstein | |
| 5,030,404 A | 7/1991 | Bonnebat et al. | |
| 5,036,110 A * | 7/1991 | Moureux | 121/137 |
| 5,036,113 A | 7/1991 | Boon et al. | |
| 5,036,603 A | 8/1991 | Dischler | |
| 5,042,176 A | 8/1991 | Rudy | |
| 5,042,781 A | 8/1991 | Ezure et al. | |
| 5,053,455 A | 10/1991 | Kroggel et al. | |
| 5,059,245 A | 10/1991 | Phillips et al. | |
| 5,090,010 A | 2/1992 | Takahashi | |
| 5,096,756 A | 3/1992 | Walters | |
| 5,157,082 A | 10/1992 | Johnson | |
| 5,181,717 A * | 1/1993 | Donntag et al. | 273/58 BA |
| 5,198,042 A | 3/1993 | Matsumoto et al. | |
| 5,215,124 A | 6/1993 | Hattori et al. | |
| 5,246,761 A | 9/1993 | Sasaki | |
| 5,292,824 A | 3/1994 | Nagai et al. | |
| 5,300,334 A * | 4/1994 | Niederst et al. | 428/35.7 |
| 5,332,767 A | 7/1994 | Reisser et al. | |
| 5,346,950 A | 9/1994 | Negi et al. | |
| 5,393,832 A | 2/1995 | Moulies et al. | |
| 5,409,041 A | 4/1995 | Yoshida et al. | |
| 5,416,988 A | 5/1995 | Potter et al. | |
| 5,429,852 A | 7/1995 | Quinn | |
| 5,436,295 A | 7/1995 | Nishikawa et al. | |
| 5,456,787 A | 10/1995 | Myles | |
| 5,458,935 A | 10/1995 | Aizner | |
| 5,462,980 A | 10/1995 | Bastioli et al. | |
| 5,489,455 A | 2/1996 | Nugent Jr. et al. | |
| 5,498,662 A | 3/1996 | Tanaka et al. | |
| 5,532,284 A | 7/1996 | Bartlett et al. | |
| 5,540,770 A | 7/1996 | Schmid et al. | |
| 5,567,489 A | 10/1996 | Allen et al. | |
| 5,578,372 A | 11/1996 | Murakami | |
| 5,591,798 A | 1/1997 | Patel | |
| 5,601,889 A | 2/1997 | Chundury et al. | |
| 5,609,962 A | 3/1997 | Ouhadi | |
| 5,612,101 A | 3/1997 | Furuta et al. | |
| 5,633,065 A | 5/1997 | Matsukura et al. | |
| 5,645,923 A | 7/1997 | Matsuo et al. | |
| 5,662,738 A | 9/1997 | Schmid et al. | |
| 5,693,424 A | 12/1997 | Watanabe et al. | |
| 5,700,560 A | 12/1997 | Kotani et al. | |
| 5,713,141 A | 2/1998 | Mitchell | |
| 6,013,340 A * | 1/2000 | Bonk et al. | 428/35.2 |

* cited by examiner

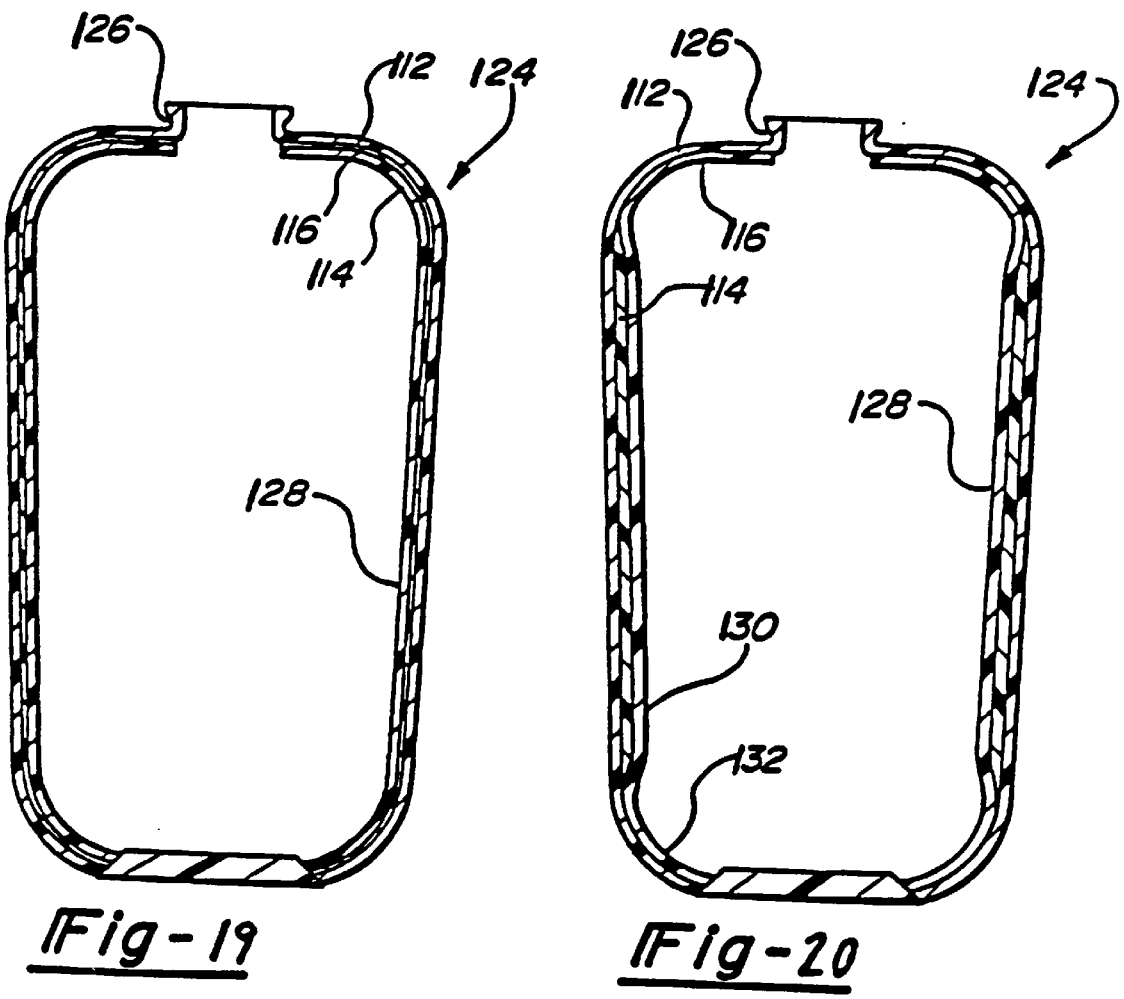

FLUID BARRIER MEMBRANES

The present application is a continuation-in-part of U.S. patent application Ser. No. 08/571,160, now U.S. Pat. No. 6,013,340, entitled "Membranes of Polyurethane Based Materials Including Polyester Polyols," filed Dec. 12, 1995, which is a continuation-in-part of U.S. patent application Ser. No. 08/475,275 abandoned, entitled "Membranes Including A Barrier Layer Employing Polyester Polyols," filed Jun. 7, 1995, both of which are hereby expressly incorporated herein by reference.

FIELD OF THE INVENTION

The invention relates to barrier membranes suitable for containing fluids and to inflated bladders made of such membranes.

BACKGROUND OF THE INVENTION

Barrier membranes and inflatable bladders formed from such membranes have been used in a variety of products such as vehicle tires, balls, accumulators used on heavy machinery, and in footwear, especially shoes, as cushioning devices. It is often desirable to use polymeric materials that are thermoplastic because thermoplastic materials may be reclaimed and reformed into new articles, thus reducing waste during manufacturing operations and promoting recycling after the life of an article. While thermoplastic barrier films may be flexed to a certain extent due to their thinness, in the past thermoplastic barrier films have generally not had sufficient elasticity for many applications. In order to overcome this shortcoming, the barrier materials were blended or layered with elastic materials. Elastic materials, or elastomers, are able to substantially recover their original shape and size after removal of a deforming force, even when the part has undergone significant deformation. Elastomeric properties are important in many applications, including inflatable bladders for footwear and hydraulic accumulators.

Footwear, and in particular shoes, usually include two major components, a shoe upper and a sole. The general purpose of the shoe upper is to snuggly and comfortably enclose the foot. Ideally, the shoe upper should be made from an attractive, highly durable, comfortable materials or combination of materials. The sole, constructed from a durable material, is designed to provide traction and to protect the foot during use. The sole also typically serves the important function of providing enhanced cushioning and shock absorption during athletic activities to protect the feet, ankles, and legs of the wearer from the considerable forces generated. The force of impact generated during running activities can amount to two or three times the body weight of the wearer, while other athletic activities such as playing basketball may generate forces of between six and ten times the body weight of the wearer. Many shoes, particularly athletic shoes, now include some type of resilient, shock-absorbent material or components to cushion the foot and body during strenuous athletic activity. These resilient, shock-absorbent materials or components are commonly referred to in the shoe manufacturing industry as the midsole. Such resilient, shock-absorbent materials or components can also be applied to the insole portion of the shoe, which is generally defined as that portion of the shoe upper directly underlying the plantar surface of the foot.

Gas-filled bladders may be used for midsoles or inserts within the soles of shoes. The gas-filled bladders are generally inflated to significant pressures in order to cushion against the forces generated on the foot during strenuous athletic activities. Such bladders typically fall into two broad categories, those that are "permanently" inflated, such as disclosed in Rudy, U.S. Pat. Nos. 4,183,156 and 4,219,945, and those using a pump and valve system, such as those disclosed in Huang, U.S. Pat. No. 4,722,131, each of which is incorporated herein by reference.

Athletic shoes of the type disclosed in U.S. Pat. No. 4,183,156 having "permanently" inflated bladders have been sold under the trademark "Air-Sole" and other trademarks by Nike, Inc. of Beaverton, Oregon. Permanently inflated bladders of such shoes are constructed using an elastomeric thermoplastic material that is inflated with a large molecule gas that has a low solubility coefficient, referred to in the industry as a "super gas." Cases such as $SF_6$, $CF_4$, $C_2F_6$, $C_3F_8$, and so on have been used in this way as super gases. Super gases are costly, however, and so it is desirable to provide permanent inflation with less expensive gasses like air or nitrogen. By way of example, U.S. Pat. No. 4,340,626 entitled "Diffusion Pumping Apparatus Self-inflating Device" which issued Jul. 20, 1982, to Rudy, which is expressly incorporated herein by reference, discloses selectively permeable sheets of film that are formed into a bladder and inflated with a gas or mixture of gases to a prescribed pressure. The gas or gases utilized ideally have a relatively low diffusion rate through the selectively permeable bladder to the exterior environment while gases contained in the atmosphere, such as nitrogen, oxygen, and argon, have a relatively high diffusion rate are able to penetrate the bladder. This produces an increase in the total pressure within the bladder, by the addition of the partial pressures of the nitrogen, oxygen and argon from the atmosphere to the partial pressures of the gas or gases with which the bladder is initially inflated. This concept of a relative one-way addition of gases to enhance the total pressure of the bladder is now known as "diffusion pumping."

Many of the earlier midsole bladders used in the footwear manufacturing industry prior to and shortly after the introduction of the Air-Sole™ athletic shoes consisted of a single layer gas barrier type film made from polyvinylidene chloride-based materials such as Saran® (which is a registered trademark of the Dow Chemical Co.) and which by their nature are rigid plastics, having relatively poor flex fatigue, heat sealability and elasticity. Composite films of two gas barrier materials have also been used. Momose, U.S. Pat. No. 5,122,322, incorporated herein by reference, describes a film of a first thermoplastic resin having a plurality of continuous tapes of a second thermoplastic resin that lie parallel to the plane of the film. The first thermoplastic resin is selected from polyolefin, polystyrene, polyacrylonitrile, polyester, polycarbonate, or polyvinyl chloride resins and modified resins. The second resin may be a polyamide, saponified ethylene vinyl acetate copolymer, ethylene-vinyl alcohol copolymer, polyvinylidene chloride, or polyacrylonitrile copolymer. The film is formed by extruding the first resin from a first extruder and the second resin from a second extruder, introducing both extrudate streams simultaneously into a static mixer in which the layers (tapes) are formed. The film may have one or two outer films laminated to it. While these films are disclosed to have an oxygen permeation rate of 0.12 to 900 cc/m²-day-atm at 20° C., making them generally suitable for forming cushioning material for packaging and shipping material, the films are not resilient or flexible enough for cushioning bladders for footwear.

Known bladder films that are composites or laminates can also present a wide variety of problems in shoe bladders, such as layer separation, peeling, gas diffusion or capillary action at weld interfaces, low elongation leading to wrinkling of the inflated product, cloudy appearing finished bladders, reduced puncture resistance and tear strength, resistance to formation via blow-molding and/or heat-sealing and RF welding, high cost processing, and difficulty with foam encapsulation and adhesive bonding, among others. Some previously known multi-layer bladders used tie-layers or adhesives in preparing laminates in order to achieve interlayer bond strength high enough to avoid the problems mentioned. The use of such tie layers or adhesives, however, generally prevents regrinding and recycling of any waste materials created during product formation back into an usable product, making manufacturing more expensive and producing more waste. Use of adhesive also increases the cost and complexity of preparing laminates. These and other perceived short comings of the prior art are described in more extensive detail in U.S. Pat. Nos. 4,340,626; 4,936,029 and 5,042,176, each of which are hereby expressly incorporated by reference.

Besides combinations of two gas barrier layers, composites may be formed from layers of materials having very different properties. Composites of different materials are particularly useful for footwear bladders because many requirements, sometimes contradictory, are made of the membranes used for footwear bladders. For instance, the membrane must exhibit excellent gas barrier properties as already mentioned toward both the inflationary gas and the ambient gases, while at the same time the membrane must be elastic and be resistant to fatigue failure. Materials used to construct footwear bladders must further be resistant to degradation from the fluids contained and from the environment to which the footwear is exposed. The problem of diverse and sometimes contradictory property requirements for membranes or films of this sort has commonly been addressed by creating laminates of at least two layers of distinct materials, one layer providing the durable flexibility of an elastomer and the other providing the fluid barrier property.

One approach has been to react or blend together at least two distinct materials to allow each of the different materials to make its respective contributions to the properties of the grafted copolymer or blend layer. Moureaux, U.S. Pat. No. 5,036,110, incorporated herein by reference, is an example of a grafted copolymer composition. Moureaux discloses a resilient membrane for a hydropnuematic accumulator that includes a film of a graft copolymer of a thermoplastic polyurethane and an ethylene vinyl alcohol copolymer. The ethylene vinyl alcohol copolymer is from 5 to 20% of the graft copolymer. The ethylene vinyl alcohol copolymer is dispersed in the polyurethane polymer and there is some grafting between the two polymers. The graft copolymer forms islands of ethylene vinyl alcohol copolymer in the polyurethane matrix. The film is a center layer between two layers of thermoplastic polyurethane in the membrane, of the hydropnuematic. While the nitrogen permeation rate is reduced as compared to unmodified polyurethane, a matrix film that includes particles of gas barrier resin does not offer a gas transmission rate as low as for a composite film that has a continuous layer of the fluid barrier material.

In an alternate approach, laminates have been described that eliminate adhesive tie layers by providing membranes including a first layer of a thermoplastic elastomer, such as a thermoplastic polyurethane, and a second layer including a barrier material, such as a copolymer of ethylene and vinyl alcohol, wherein hydrogen bonding occurs over a segment of the membranes between the first and second layers. Such laminates with layers of flexible materials and layers of fluid barrier materials are described, for example, in U.S. Pat. No. 5,713,141, issued Feb. 3, 1998, incorporated herein by reference, and in copending U.S. applications Ser. No. 08/299,287, filed Aug. 31, 1994, entitled "Cushioning Device with Improved Flexible Barrier Membrane;" Ser. No. 08/684,351, filed Jul. 19, 1996, entitled "Laminated Resilient Flexible Barrier Membranes;" Ser. No.08/475,276, filed Jun. 7, 1995, entitled "Barrier Membranes Including a Barrier Layer Employing Aliphatic Thermoplastic Polyurethanes;" Ser. No.08/475,275, filed Jun. 7, 1995, entitled "Barrier Membranes Including a Barrier Layer Employing Polyester Polyols;" and Ser. No. 08/571,160, filed Dec. 12, 1995, entitled "Membranes of Polyurethane Based Materials Including Polyester Polyols," each of which is incorporated herein by reference. While the membranes disclosed in these references provide flexible, "permanently" inflated, gas-filled shoe cushioning components that are believed to offer a significant improvement in the art, still further improvements are offered according to the teachings of the present invention.

It would therefore be desirable to produce a barrier membrane from a material having a desirably gas transmission rate without the problems of delamination and inadequate flexibility associated with previously known barrier membranes and laminate membranes with layers including barrier materials.

SUMMARY OF THE INVENTION

The present invention provides a barrier membrane in which the polymeric component that provides the barrier properties is a thermoplastic polyester-modified polyurethane. The polyester portion of the polyester-modified polyurethane material of the invention has repeating units in which the total number of carbon atoms is about eight or less.

The invention further provides a bladder having walls formed of the barrier membrane of the invention. The bladder may be inflated with a gas such as nitrogen, air, or a supergas and used as an inflating bladder or cushioning device, especially in footwear. The barrier membrane as a gas transmission rate that is sufficiently low to allow the bladder to remain "permanently" inflated, that is, to retain a useful internal pressure for the useful life of the footwear.

The invention further provides a hydropneumatic accumulator comprising the barrier membrane of the invention.

It is an object of the invention to provide membranes and membrane material that offer enhanced flexibility and resistance to undesirable transmission of fluids such as an inflationary gas. It is another object of the invention to provide elastic membranes for inflatable bladders that can be inflated with a gas such as nitrogen, in which the membrane provides a gas transmission rate value of about 10 cubic centimeters per square meter per atmosphere per day (cc/$m^2$·atm·day) or less. It is further an object of the invention to provide a barrier membrane resistant to interlayer delamination.

The polymeric barrier material of the invention may be used to form a durable, elastomeric membrane for pressurized bladders and other cushioning devices to be used in many applications, particularly in footwear or for accumulators. By "durable" it is meant that the membrane has excellent resistance to fatigue failure, which means that the membrane can undergo repeated flexing and/or deformation and recover without delamination along the layer interfaces of composite barrier membranes, preferably over a broad range of temperatures. For purposes of this invention, the term "membrane" is used to denote preferably a freestanding film separating one fluid (whether gas or liquid) from another fluid. Films laminated or painted onto another article for purposes other than separating fluids are preferably excluded from the present definition of a membrane.

In particular, the present invention provides an inflatable bladder for applications such as footwear or hydraulic accumulators, the bladder having a membrane that includes at least one layer of the polyester-modified polyurethane barrier material of the invention. The membrane of the invention has elastomeric mechanical properties that allows it to repeatedly and reliably absorb high forces during use without degradation or fatigue failure. It is particularly important in applications such as footwear and hydraulic accumulator for the membrane to have excellent stability in cyclic loading. The barrier membrane has a low gas transmission rate provided by the polyester-modified polyurethane barrier material that allows it to remain inflated, and thus to provide cushioning, for substantially the expected life of the footwear or hydraulic accumulator without the need to periodically re-inflate and re-pressurize the bladder.

The nitrogen gas transmission rate of the membrane should be less than about 10 cubic centimeters per square meter per atmosphere per day ($cc/m^2 \cdot atm \cdot day$). An accepted method of measuring the relative permeance, permeability and diffusion of different film materials is set forth in the procedure designated as ASTM D-1434-82-V. According to ASTM D-1434-82-V, permeance, permeability and diffusion are measured by the following formulas:

Permeance (quantity of oas)/[(aroa)×(time)×(press. diff.)]= Permeance (GTR)/(press. diff.)=cc/(sq.m)(24hr)(Pa)

Permeability

[(quantity of gas)×(film thickness)]/[(area)×(time)×(press.diff.)]=Permeability [(GTR)×(film thick.)]/(press.diff.)=[(cc)(mil)]/[($m^2$)(24hr)(Pa)]

Diffusion (at one atmosphere)

(quantity of gas)/[(area)×(time)]=Gas Transmission Rate (GTR)=cc/($m^2$)(24hr)

BRIEF DESCRIPTION OF THE DRAWINGS

FIG. 19 is a sectional view of a product formed from a laminated membrane according to the teachings of the present invention;

FIG. 20 is a sectional view of a second product manufactured using a laminated membrane according to the teachings of the present invention;

DETAILED DESCRIPTION OF THE INVENTION

Figure 1:
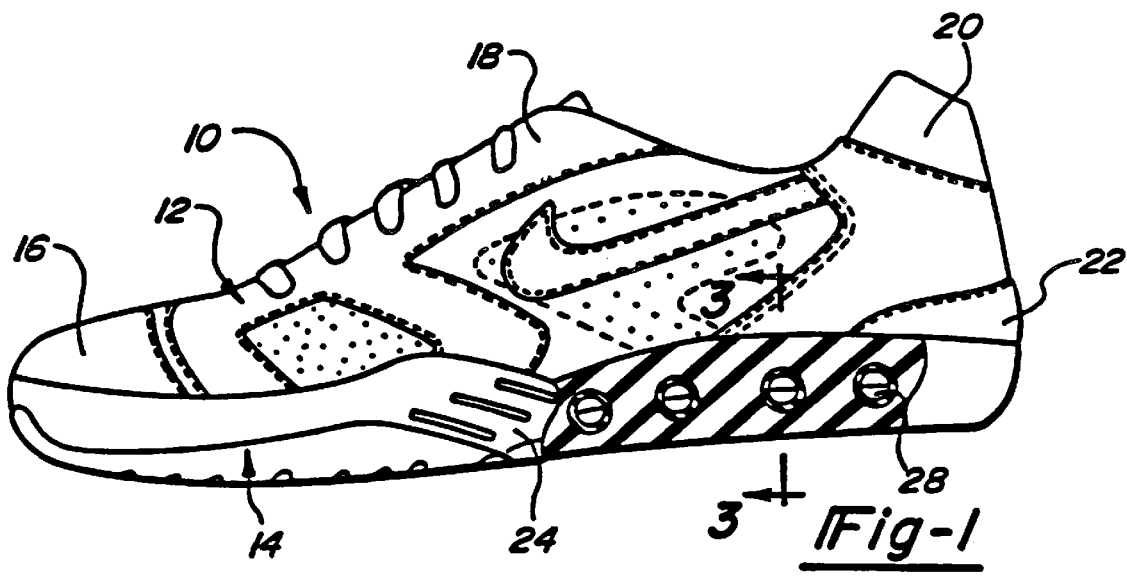
FIG. 1 is a side elevational view of an athletic shoe with a portion of the midsole cut away to illustrate a cross-sectional view.

The fluid barrier membrane of the invention includes as the component providing the barrier properties a polyester-modified polyurethane material in which the polyester segment(s) has repeating units of about eight or fewer carbon atoms. The polyester segments are formed by reaction of at least one diol and at least one diacid. By "repeating units," we mean an ester unit having the residue of one diol and the residue of one diacid and their respective portions of the linking ester groups. A repeating unit may be expressed structurally as

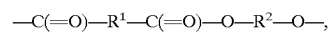

—C(=O)—R$^1$—C(=O)—O—R$^2$—O—, in which R$^1$ is an alkylene of from 0 (for oxalic acid) to about 5 carbon atoms, and R$^2$ is an alkylene of from about 2 to about 6 carbon atoms. The carbonyl carbons and the carbons of R$^1$ together represent the carbon atoms of the residue of the dicarboxyliG acid. It is known that polyesters may be made using more than one dicarboxylic acid and/or more than one diol. In that case, not every repeating unit would be the same, but the polyester would have about eight or fewer carbon atoms per repeating unit, on average, and preferably about eight or fewer carbons atoms for each individual dicarboxylic acid-diol repeating unit.

The polyester diol that is used to form the polyester-modified polyurethane is polymerized under typical reaction conditions by reacting at least one diol with at least one dicarboxylic acid or anhydride. The polyester diols used in forming the preferred thermoplastic polyurethane of the invention are in general prepared by the condensation polymerization of polyacid compounds or anhydrides thereof and polyol compounds. Preferably, the polyacid compounds and polyol compounds are all di-functional, i.e., diacid compounds or anhydrides of diacids and diols are used to prepare substantially linear polyester diols, although minor amounts of mono-functional, tri-functional, and higher functionality materials (perhaps up to 5 mole percent) can be included. Suitable diols include any of those aliphatic diols having about 6 or fewer total carbon atoms. Particular examples of suitable diols include, without limitation, alkylene glycols having up to about 6 carbon atoms, such as ethylene glycol, diethylene glycol, triethylene glycol, propylene glycol, dipropylene glycol, and butylene glycol; α,ω-alkanediols of up to about 6 carbon atoms, such as 1,3-propanediol, 1,4-butanediol, and 1,6-hexanediol; and other diol isomers, such as 1,3-butanediol, 2,3-butanediol, 1,3-pentanediol, 2,3-pentanediol, neopentyl glycol, 1,3-cyclopentanediol, 1,4-cylcohexanediol, 3,3-dimethyl-1,2-butanediol, 2-ethyl-2-methyl-1,3-propanediol, 2-methyl-2,4-pentanediol, 5-hexene-1,2-diol, 2-propyl-1,3-propanediol, pinacol, and so on; as well as combinations of these. Preferred diols include ethylene glycol, propylene glycol, neopentyl glycol, and combinations of these. The polyol portion may also include a minor amount of a higher functionality polyol, such as trimethylolpropane or glycerol, preferably in an amount of less than about 5% by weight of the polyester reactant, and more preferably less than about 2% of the polyol reactant. In a particularly preferred embodiment the polyester is linear, e.g., only diols are used.

Suitable dicarboxylic acids and anhydrides include, without limitiaton, oxalic acid, malonic acid, diglycolic acid, maleic acid, fumaric acid, citraconic acid glutaconic acid, itaconic acid, mesaconic acid, succinic acid, methylsuccinic acid, muconic acid, glutaric acid, adipic acid, pimelic acid, dimethylsuccinic acid, methylglutaric acid, cyclopentanedicarboxylic acid, butylmalonic acid, diethylmalonic acid, dimethylglutaric acid, methyladipic acid, ethylmethylsuccinic acid, and anhydrides thereof, as well as combinations of these acids and anhydrides. Preferred dicarboxylic acids include glutaric acid, succinic acid, malonic acid, maleic acid, and adipic acid, anhydrides thereof, and combinations of these acids and anhydrides. In particular, combinations of ethylene glycol with adipic acid, glutaric acid, succinic acid, or anhydrides thereof are preferred.

The polyester diol may be prepared under typical reaction conditions for polyesters. Typical catalysts for the esterification polymerization are protonic acids, Lewis acids, titanium alkoxides, and dialkyltin oxides, although others are known and useful. The diol or polyol portion is included in an equivalent excess to form the polyester diol. The polyester diol has a number average molecular weight (determined for example by the ASTM D-4274 method) of preferably at least about 300, more preferably at least about 500, and even more preferably at least about 750. The polyester diol may have a number average molecular weight of up to about 5000, more preferably up to about 2000, and even more preferably up to about 1500. In a preferred embodiment, the polyester diol has a number average molecular weight of from about 300 to about 5000, more preferably from about 500 to about 2000, and even more preferably from about 750 to about 2000.

The polyester-modified polyurethane that provides the barrier properties in the barrier membrane of the invention may be formed by reaction of the polyester diol with at least one diisocyanate and, optionally, with one or more extender compounds (or chain extension agents) having two isocyanate-reactive functionalities. The diisocyanate may be selected from aromatic, aliphatic, and cycloaliphatic diisocyanates and combinations thereof. Representative of useful diisocyanates include m-phenylene diisocyanate, 2,4-toluene diisocyanate, 2,6-toluene diisocyanate, mixtures of 2,4- and 2,6-toluene diisocyanate, hexamethylene diisocyanate, tetramethylene diisocyanate, cyclohexane-1,4-diisocyanate, any of the isomers of hexahydrotoluene diisocyanate, isophorone diisocyanate, any of the isomers of hydrogenated diphenylmethane diisocyanate (methylene-bis-cyclohexyl isocyanate), naphthalene-1,5-diisocyanate, 1-methoxyphenyl-2,4-diisocyanate, any of the isomers of diphenylmethane diisocyanate, including 2,2'-diphenylmethane diisocyanate, 2,4'-diphenylmethane diisocyanate, and 4,4'-diphenylmethane diisocyanate, isomers of biphenylene diisocyanate including 2,2'-, 2,4'-, and 4.4'-biphenylene diisocyanates, 3,3'-dimethoxy-4,4'-biphenyl diisocyanate and 3,3'-dimethyl-diphenylmethane-4,4'-diisocyanate, isomers of tetramethylxylene diisocyanate (including m-TMXDI and p-TMXDI), xylylene diisocyanate, and combinations thereof. In one embodiment, the diisocyanate includes a diphenylmethane diisocyanate or mixtures of isomers thereof. Polyisocyanates having more than two isocyanate groups such as 1,2,4-benzene triisocyanate may be included at low levels, but it is preferred to use only diisocyanates.

Preferably, the reaction of the polyester diol and the diisocyanate further includes one or more extender molecules that have two groups reactive with isocyanate functionality selected from active hydrogen-containing groups such as primary amine groups, secondary amine groups, and thiol, and hydroxy groups. The molecular weight of the chain extenders preferably range from about 60 to about 400. Alcohols and amines are preferred. Useful examples of extender compounds include, without limitation, diols, dithiols, diamines, or compounds having a mixture of hydroxyl, thiol, and primary or secondary amine groups, such as aminoalcohols, aminoalkyl mercaptans, and hydroxyalkyl mercaptans. Particular examples of such materials include, without limitation, ethylene glycol, diethylene glycol, and higher polyethylene glycol analogs like triethylene glycol; propylene glycol, dipropylene glycol, and higher polypropylene glycol analogs like tripropylene glycol; 1,3-propanediol, 1,4-butanediol, 1,3-butanediol, 1,6-hexanediol, 1,7-heptanediol, neopentyl glycol, dihydroxyalkylated aromatic compounds such as 4,4'-isopropylidene diphenol, (bisphenol A), resorcinol, catechol, hydroquinone, benzenedimethanols, the bis (2-hydroxyethyl) ethers of hydroquinone and resorcinol; p-xylene-α,α'-diol; the bis (2-hydroxyethyl) ether of p-xylene-α,α'-diol; m-xylene-α, α'-diol and the bis (2-hydroxyethyl) and alkylene oxide adducts of such diols; diethyl toluene diamine, polyalkylpolyamines such as ethylenediamine, diethylenetriamine, and triethylenetetramine, difunctional polyoxyalkylene amines (available commercially under the tradename POLYAMINE® from BASF Corporation or under the tradename JEFFAMINE® from Huntsman), methylenedianiline p-phenylenediamine, m-phenylenediamine, benzidine, 4,4'-methylenibis (2-chloroaniline), alkanolamines and alkylalkanolamines such as ethanolamine, propanolamine, butanolamine, methylethanolamine, ethylethanolamine, methylpropanolamine, tert-butylaminoethanol, and combinations thereof. Preferred extenders include ethylene glycol, diethylene glycol, triethylene glycol, tetraethylene glycol, propylene glycol, dipropylene glycol, tripropylene glycol, tetrapropylene glycol, 1,3-propylene glycol, 1,4-butanediol, 1,6-hexanediol, and combinations of these. In addition to the difunctional extenders, a small amount of trifunctional extenders such as trimethylol propane, 1,2,6-hexanetriol and glycerol, and/or monofunctional active hydrogen compounds such as butanol or dimethyl amine, may also be present. The amount of trifunctional extenders and/or monofunctional compounds employed would preferably be 5.0 equivalent percent or less based on the total weight of the reaction product and active hydrogen containing groups employed.

The polyurethane includes at least about 25% weight percent of segments of the polyester polyol according to the invention that has repeating units of eight or fewer carbon atoms. In a preferred embodiment, the polyurethane includes at least about 35 weight percent of the polyester segments, and it is even more preferred that the polyurethane includes at least about 40 weight percent of the polyester segments. The polyester-modified polyurethane may include up to about 80 weight percent of the polyester segments, preferably up to about 65 weight percent of the polyester segments, and even more preferably up to about 60 weight percent of the polyester segments. The polyester-modified polyurethane may include from about 25 to about 80 weight percent of the polyester segments, preferably from about 35 to about 65 weight percent of the polyester segments, and even more preferably from about 40 to about 60 weight percent of the polyester segments.

Generally, the ratio of equivalents of polyester diol to equivalents of extender compound(s) can be varied. Preferably, the ratio of equivalents of polyester diol to equivalents of extender is from about 1:1 to about 1:12, more preferably from about 1:1 to about 1:8. The ratio of equivalents of polyisocyanate, which is preferably all diisocyanate, to combined equivalents of polyester diol and extender ranges from about 0.96 to about 1.05 equivalent of isocyanate to 1 equivalent of the combined polyester diol and extender. More preferred is a range of from about 0.98 to about 1.04 equivalents of isocyanate per equivalent of combined polyester diol and extender and even more preferred is a range of about 1.001 to about 1.01 equivalent of isocyanate to 1 equivalent of the combined polyester diol and extender.

The barrier composition may include further polymeric or oligomeric components that do not provide barrier properties but may advantageously added to affect other physical properties. Such polymeric materials may be included in amounts of up to about 20% by weight of the total polymeric component of the composition. Suitable examples include non-barrier polyester-polyurethanes, polyamide-ether elastomers marketed under the tradename PEBAX® by Elf Atochem, ester-ether elastomers marketed under the tradename HYTREL® by DuPont, ester-ester and ester-ether elastomers marketed under the tradename ARNITEL® by DSM Engineering, thermoplastic vulcanizates marketed under the tradename SANTOPRENE® by Advanced Elastomeric Systems, elastomeric polyamides marketed under the tradename GRILAMID® by Emser, and elastomeric polyurethanes marketed under the tradename PELLETHANE® by Dow Chemical Company, Midland, Mich., ELASTOLLAN® polyurethanes marketed by BASF Corporation, Mt. Olive, N.J. TEXIN® and DESMOPAN® polyurethanes marketed by Bayer, MORTHANE® polyurethanes marketed by Morton, and ESTANE® polyurethanes marketed by B.F. Goodrich Co.;

The barrier membrane or the layer of the barrier membrane in which the polyester-modified polyurethane provides the barrier property may contain other components, either polymeric or non-polymeric. Examples of such materials include, without limitation, hydrolytic stabilizers, plasticizers, antioxidants, UV stabilizers, thermal stabilizers, light stabilizers, organic anti-block compounds, colorants (including pigments, dyes, and the like), fungicides, antimicrobials (including bacteriocides and the like), mold release agents, waxes such as Montan esters or bis-amide waxes, processing aids, and combinations of these. Transparent, substantially colorless membranes may be formed by omitting any colorants. Tinted transparent membranes may also be formed with transparent colorants. Inorganic fillers such as mica or talc may be included in amounts of up to about 40% by weight.

Examples of hydrolytic stabilizers include two commercially available carbodiimide based hydrolytic stabilizers known as STABAXOL P and STABAXOL P-100, which are available from Rhein Chemie of Trenton, N.J. Other carbodiimide- or polycarbodiimide-based hydrolytic stabilizers or stabilizers based on epoxidized soy bean oil may be useful. The total amount of hydrolytic stabilizer employed will generally be less than 5.0 wt. % of the composition's total.

Plasticizers can be included for purposes of increasing the flexibility and durability of the final product as well as facilitating the processing of the material from a resinous form to a membrane or sheet. By way of example, and without intending to be limiting, plasticizers such as those based on butyl benzyl phthalate (which is commercially available, e.g. as Santicizer 160 from Monsanto) have proven to be particularly useful. Regardless of the plasticizer or mixture of plasticizers employed, the total amount of plasticizer, if any, will generally be less than 20.0 wt. % of the total composition, typically less than about 5% by weight of the total composition.

The membrane of the invention includes the polyester-modified polyurethane barrier layer, either as an only layer or as one layer in a laminate construction. The membrane may be of any convenient length and width for forming the desired cushioning or pressurized bladder, such as the footwear bladder or hydraulic accumulator. The average thickness of the polyester-modified polyurethane layer may vary widely, but it may be, for example, from about 3 mils (about 75 microns) to about 200 mils (about 0.5 cm). Preferably, the average thickness of the barrier layer of polyester-modified polyurethane is at least about 50 microns, preferably from about 75 microns to about 0.5 cm, more preferably from about 125 microns to about 0.5 cm, and particularly preferably from about 125 microns to about 0.15 cm. When the barrier layer of polyester-modified polyurethane is to be used to prepare a bladder for footwear it is preferred that the layer have an average thickness of from about 3 mils (about 75 microns) to about 40 mils (about 0.1 cm), while membranes used in hydropneumatic accumulators are usually thicker. In one preferred embodiment the barrier layer of polyester-modified polyurethane has an average thickness of at least about 125 microns.

The membrane of the invention can be a laminate that includes the polyester-modified polyurethane layer as one or more laminate layers. Preferably, the alternate layers are selected from polyurethane or modified polyurethane materials. Any number of the polyester-modified polyurethane barrier layers, preferably from one to about 5, more preferably one to three are used as alternate layers of the laminate. The other layers of the laminate preferably as elastomeric and include thermoplastic elastomers. When the barrier layer of the invention is used to prepare a laminate, the laminate may have an average thickness of from about 3 mils (about 75 microns) to about 400 mils (about 1 cm), and preferably it has an average thickness of from about 100 mils (about 0.25 microns) to about 200 mils (about 0.5 cm).

The membranes and bladders or cushioning devices of the invention may be formed by a number of methods. Among these techniques known in the art are extrusion, blow molding, injection molding, vacuum molding, transfer molding, pressure forming, heat-sealing, casting, melt casting, and RF welding and so on. A bladder may be produced by RF (radio frequency) welding two sheets of the barrier material. Other well-known welding techniques may also be employed.

The bladder or cushioning device may be inflated with air or components of air such as nitrogen, or with supergases. When used as cushioning devices in footwear such as shoes, the bladder may be inflated, preferably with nitrogen, to an internal pressure of at least about 3 psi, preferably at least about 5 psi, and up to about 50 psi. Preferably the bladder is inflated to an internal pressure of from about 5 psi to about 35 psi, more preferably from about 5 psi to about 30 psi, still more preferably from about 10 psi to about 30 psi, and yet more preferably from about 10 psi to about 25 psi. It will be appreciated by the skilled artisan that in applications other than footwear applications the desired and preferred pressure ranges may vary dramatically and can be determined by those skilled in that particular field of application. Accumulator pressures, for example, can range up to perhaps 1000 psi. Accumulator pressures are preferably up to about 500 psi. A preferred range of pressure for accumulator applications is from about 200 psi to about 1000 psi, but pressures as low as about 25 psi are possible depending upon the design of the accumulator.

Preferably, the membranes described herein may be useful for forming cushioning components for footwear. In such applications, the membranes preferably are Gapable of containing a captive gas for a relatively long period of time. In a highly preferred embodiment, for example, the membrane should not lose more than about 20% of the initial inflated gas pressure over a period of approximately two years. In other words, products inflated initially to a steady state pressure of between 20.0 to 22.0 psi should retain pressure in the range of about 16.0 to 18.0 psi for at least about two years.

The inflationary gas transmission rate of the material for the inflationary gas, which is preferably nitrogen gas, should be less than 10 cubic centimeters per square meter per atmosphere per day ($cc/m^2 \cdot atm \cdot day$), preferably less than about 3 a $cc/m^2 \cdot atm \cdot day$, and particularly preferably less than about 2 $cc/m^2 \cdot atm \cdot day$.

Figure 2:
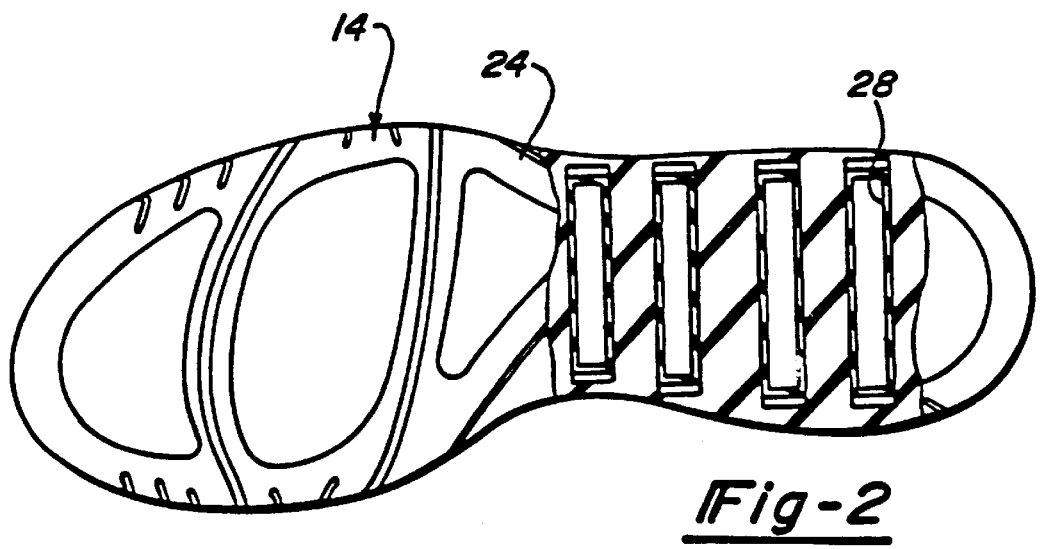
FIG. 2 is a bottom elevational view of the athletic shoe of FIG. 1 with a portion cut away to expose another cross-sectional view.
Figure 3:
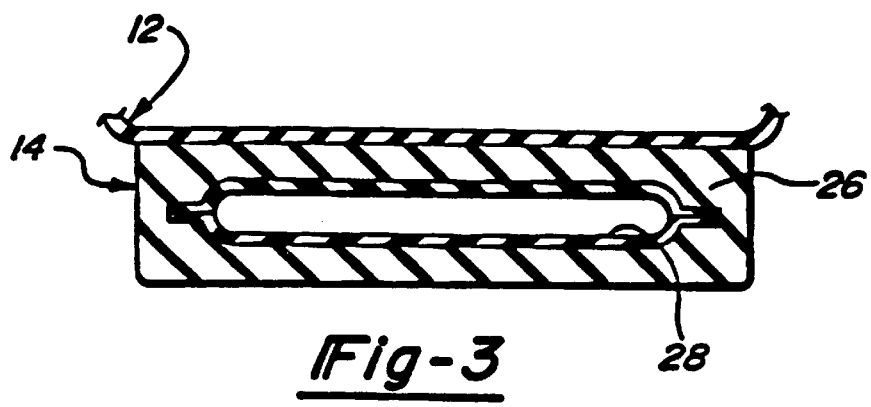
FIG. 3 is a section view taken alone line 3—3 of FIG. 1.

Referring to FIGS. 1–3, there is shown an athletic shoes including a sole structure and a cushioning device as one example of a product formed from a membrane in accordance with the teachings of the present invention. The shoe 10 includes a shoe upper 12 to which the sole 14 is attached. The shoe upper 12 can be formed from a variety of conventional materials including, but not limited to, leathers, vinyls, and nylons and other generally woven fibrous materials. Typically, the shoe upper 12 includes reinforcements located around the toe 16, the lacing eyelets 18, the top of the shoe 20 and along the heel area 22. As with most athletic shoes, the sole 14 extends generally the entire length of the shoe 10 from the toe region 20 through the arch region 24 and back to the heel portion 22.

Figure 4:
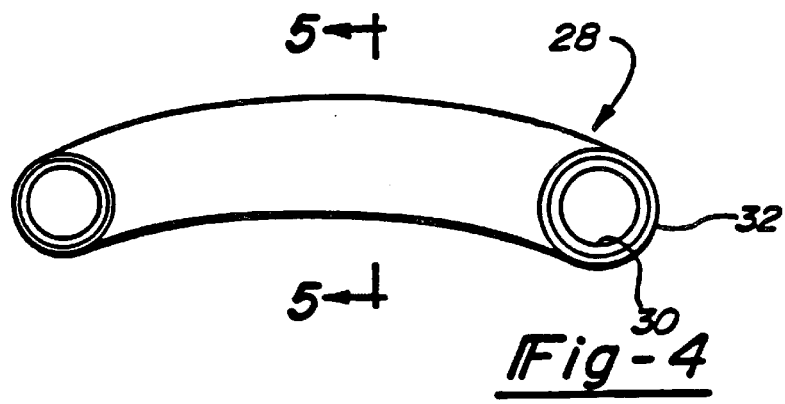
FIG. 4 is a fragmentary side perspective view of one embodiment of a tubular-shaped, two-layer cushioning device.
Figure 5:
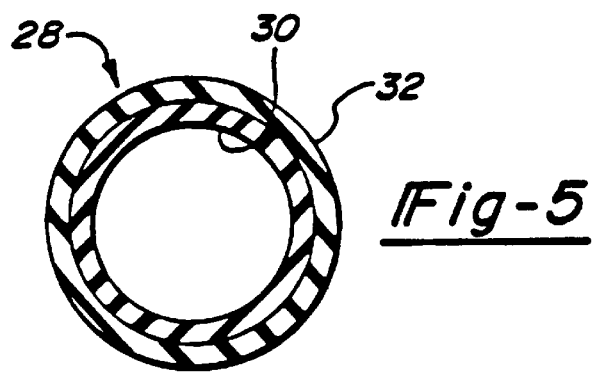
FIG. 5 is a sectional view taken along line 4—4 of FIG. 4.
Figure 24:
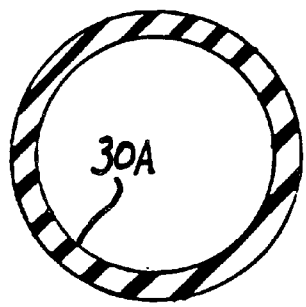
FIG. 24 is a sectional view of a monolayer tubular membrane.

The sole structure 14 is shown to include one or more cushioning devices or bladders 28 according to the invention, which are generally disposed in the midsole of the sole structure. By way of example, the membranes 28 of the present invention can be formed into products having various geometries such as a plurality of tubular members which are positioned in a spaced apart, parallel relationship to each other within the heel region 22 of the midsole 26 as illustrated in FIGS. 1–3. The tubular members are sealed to contain an injected captive gas. The barrier properties of the membrane 28 may be provided by a single layer of the polyester-modified polyurethane barrier material 30A as shown in FIG. 24 or by the polyester-modified polyurethane barrier material layer 30 as shown in FIGS. 4–5 which is disposed along the inner surface of a thermoplastic elastomer outer layer 32. As illustrated in FIGS. 8–18, the membranes 28 of the present invention, whether monolayer or multi-layer embodiments, can be formed into a variety of products having numerous configurations or shapes. As should be appreciated at this point, membranes 28 which are formed into cushioning devices employed in footwear may either be fully or partially encapsulated within the midsole or outsole of the footwear. The bladder is thus incorporated as a portion of the sole and may form at least a part of an outer surface of the shoe at the sole.

Referring again to FIGS. 1–3, a membrane 28 in accordance with teachings of the present invention is illustrated as being in the form of a cushioning device such as those useful as components of footwear. The membrane 28, according to the embodiment illustrated in FIG. 24, comprises a single layer 30A of a polyester-modified polyurethane barrier material.

Figure 6:
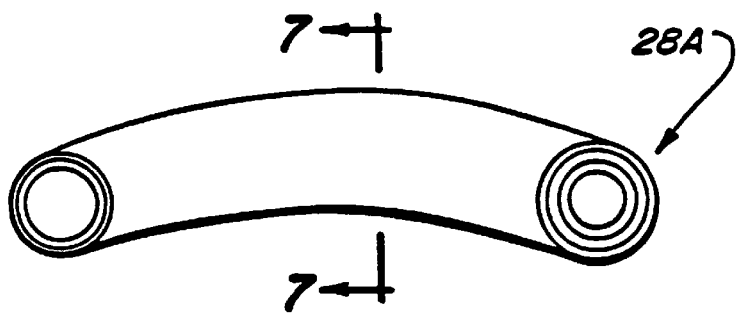
FIG. 6 is a fragmentary side perspective view of a second embodiment of a tubular-shaped, three-layer cushioning device.
Figure 7:
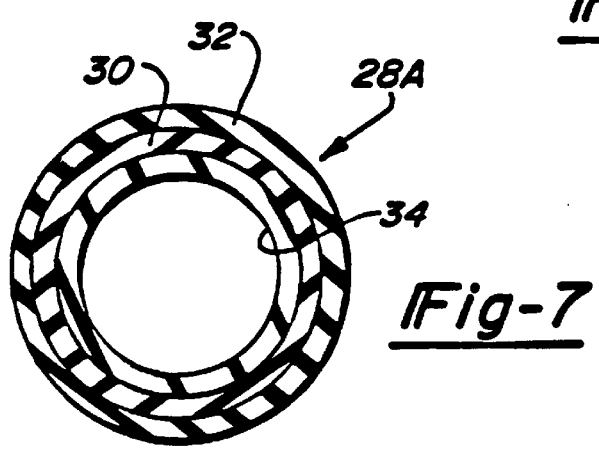
FIG. 7 is a sectional side view taken along line 6—6 of FIG. 6.

Referring now to FIGS. 6 and 7, an alternative membrane embodiment A in the form of an elongated tubular shaped multi-layered component is illustrated. The modified membrane A is essentially the same as the membrane 28 illustrated in FIGS. 4 and 5 except that a third layer 34 is provided contiguously along the inner surface of the layer 30, such that layer 30 is sandwiched between an outer layer 32 and an innermost layer 34. The innermost layer 34 is also preferably made from a thermoplastic polyurethane material. In addition to the perceived benefit of enhanced protection against degradation of layer 30, layer 34 also tends to assist in providing for high quality welds which facilitate the formation of three-dimensional shapes for products such as cushioning devices useful in footwear. Not shown but preferred is an elongated tubular shaped component that is a single layer of the polyester-modified polyurethane barrier material.

Membranes such as those shown in FIGS. 1–7 and FIG. 24 are preferably fabricated from extruded tubes. Lengths of the tubing are continuously extruded and typically spooled in about fifty feet lengths when manufactured for inflatable bladders for footwear. Sections of the tubing are RF welded or heat sealed to the desired lengths. The individual sealed inflatable bladders produced upon RF welding or heat sealing are then separated by cutting through the welded areas between adjacent bladders. The bladders can then be inflated to a desired initial inflation pressure ranging from 3 psi ambient to 100 psi, preferably in the range of 3 to 50 psi, with the captive gas preferably being nitrogen. It should also be noted that the bladders can be fabricated from so-called flat extruded tubing as is known in the art with the internal geometry being welded into the tube.

Figure 8:
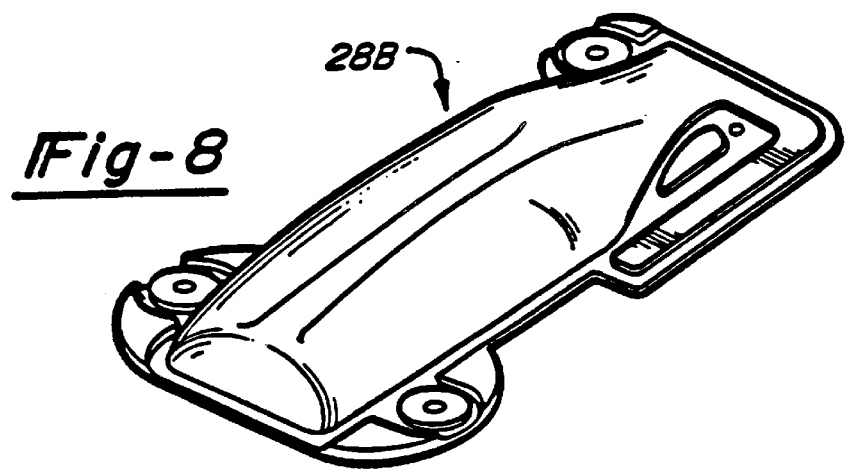
FIG. 8 is a perspective view of a membrane embodiment according to the present invention formed into a shoe cushioning device.
Figure 9:
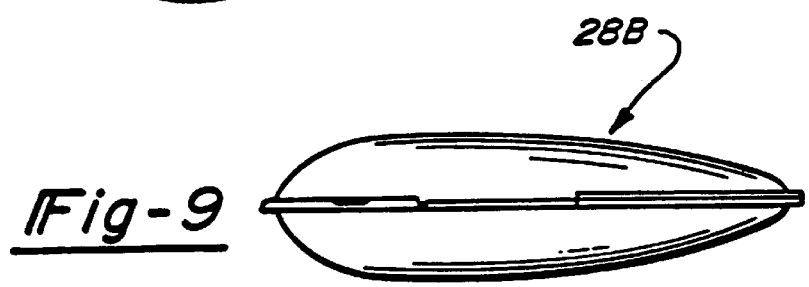
FIG. 9 is a side view of the membrane illustrated in FIG. 8.
Figure 10:
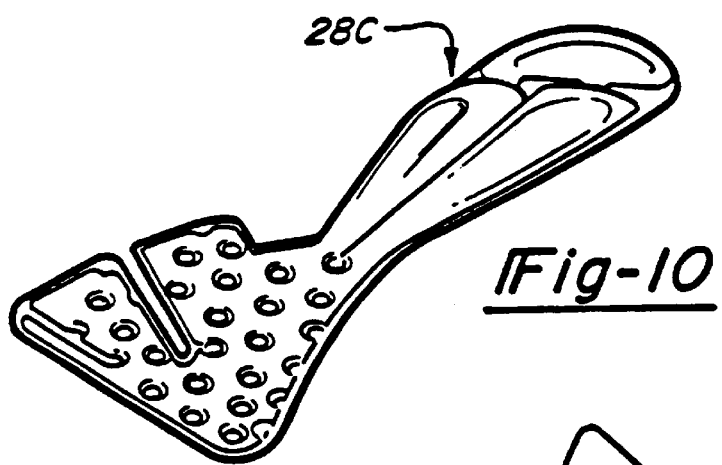
FIG. 10 is a perspective view of a membrane embodiment according to the present invention formed into a shoe cushioning device.
Figure 11:
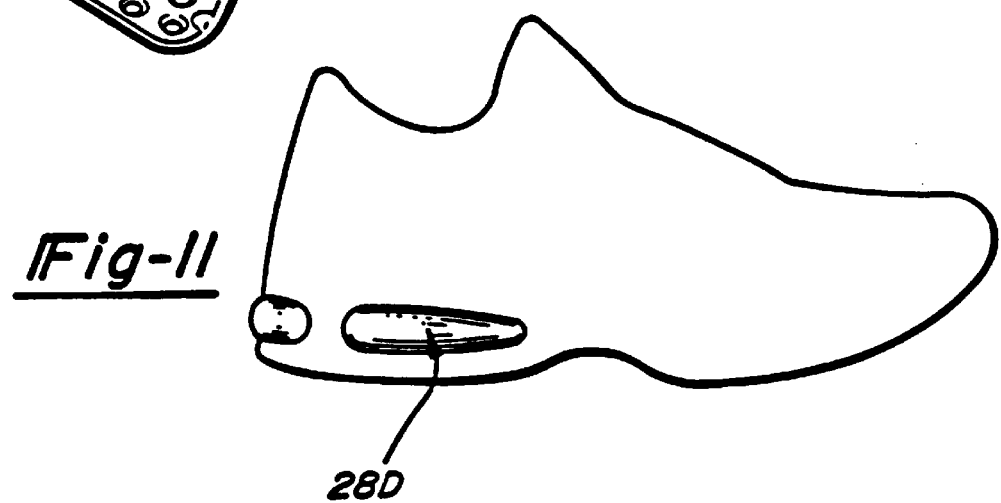
FIG. 11 is a side elevational view of a membrane embodiment according to the present invention formed into a cushioning device which is incorporated into a shoe.

Other embodiments formed from the membranes described herein are shown in FIGS. 8–10. Sheets or films of extruded monolayer membrane are formed to the desired thicknesses. For example, the thickness range of the membrane is preferably between about 5 mils to about 60 mils and, more preferably, between about 15 mite and to about 40 mils.

Figure 12:
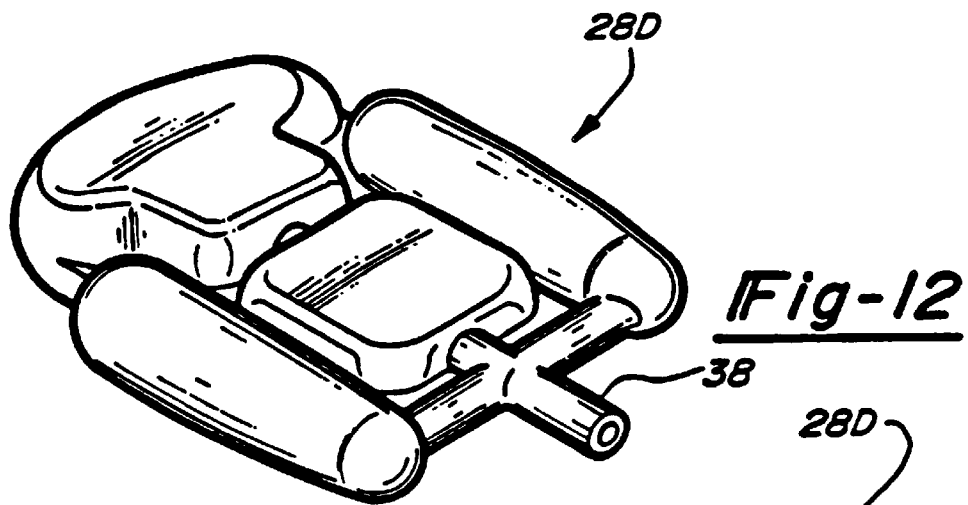
FIG. 12 is a perspective view of the membrane illustrated in FIG. 11.
Figure 13:
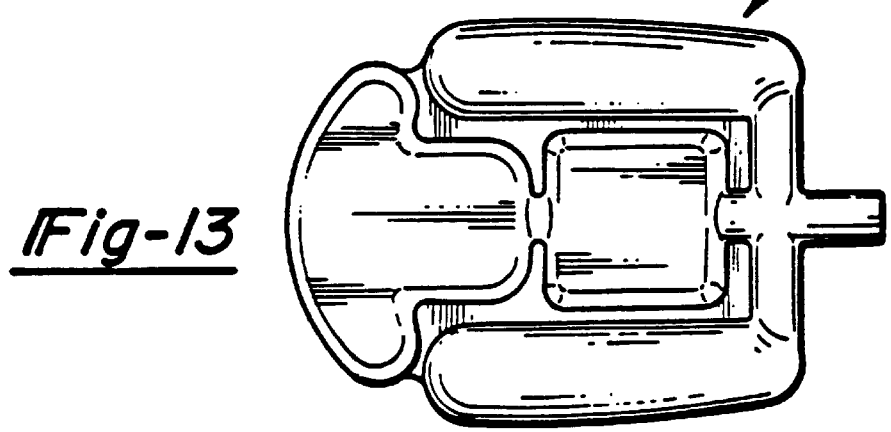
FIG. 13 is a top elevation view of the membrane illustrated in FIGS. 11 and 12.
Figure 14:
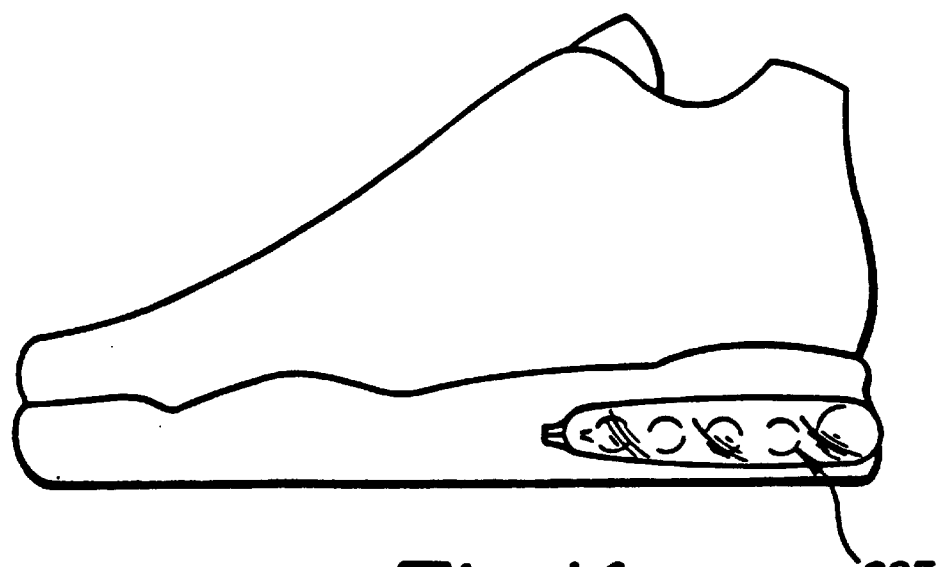
FIG. 14 is a side elevation view of a membrane embodiment according to the present invention formed into a cushioning device incorporated into a shoe.
Figure 15:
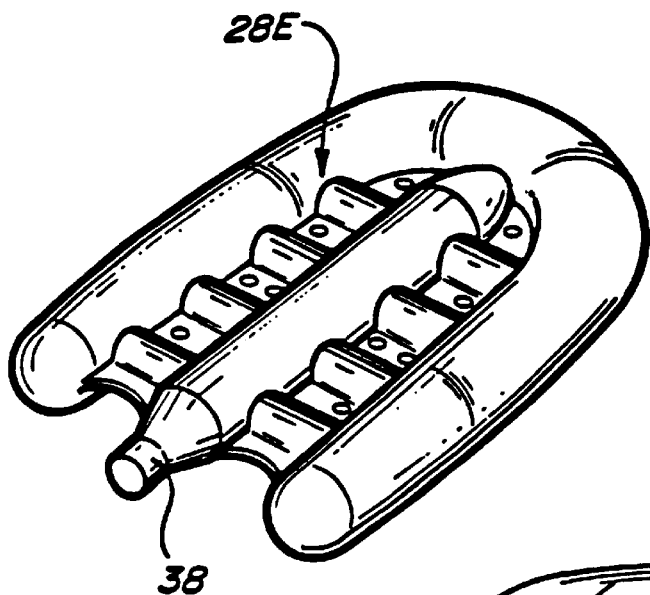
FIG. 15 is a perspective view of the membrane illustrated in FIG. 14.
Figure 16:
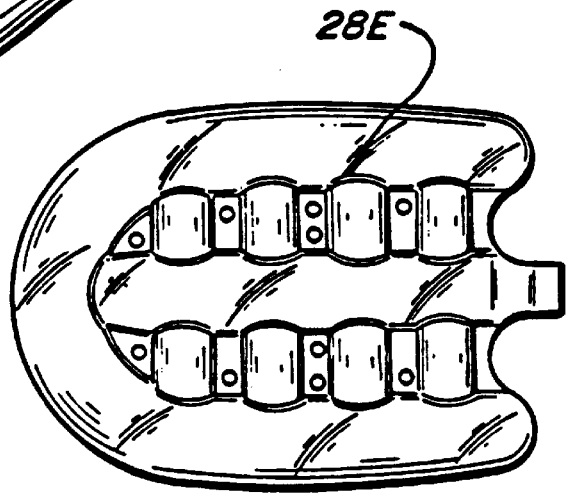
FIG. 16 is a top view of the membrane illustrated in FIGS. 14 and 15.
Figure 21:
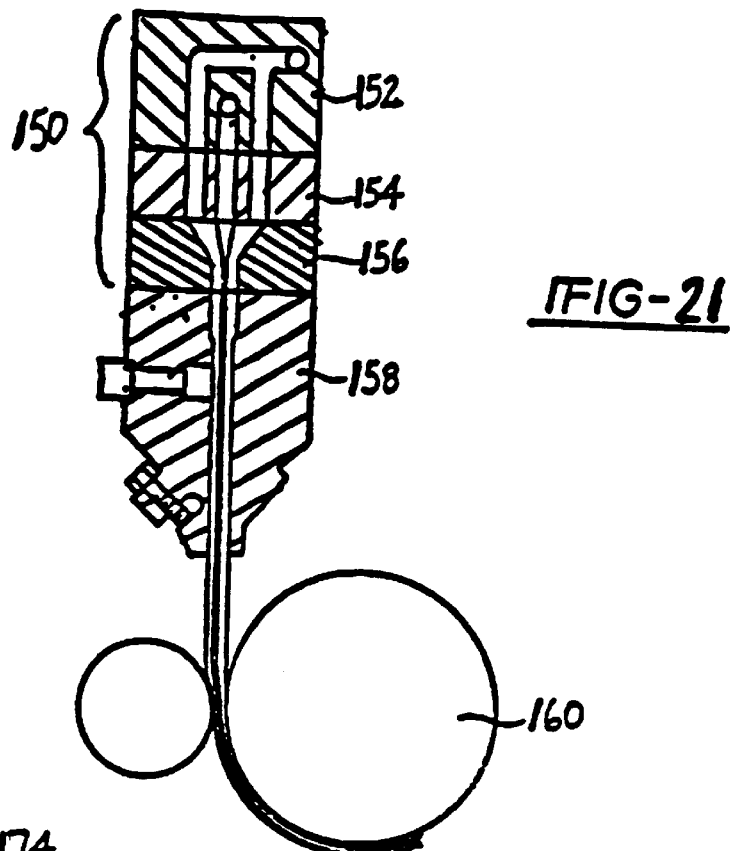
FIG. 21 is a side elevation view of a sheet co-extrusion assembly.
Figure 23:
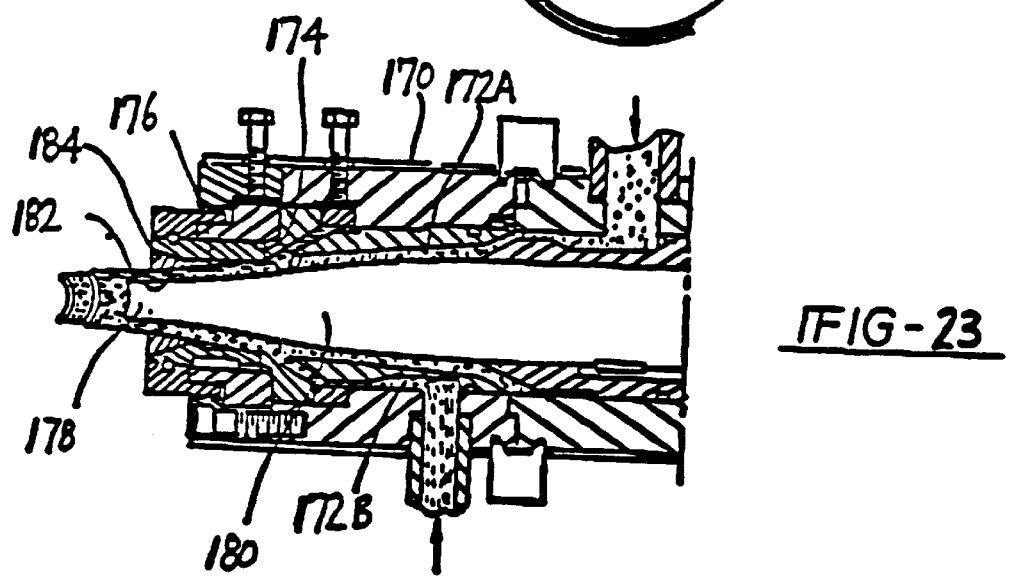
FIG. 23 is a side elevation view of a tubing co-extrusion assembly.
Figure 22:
FIG. 22 is a cross-sectional view of the manifold portion of the sheet co-extrusion assembly of FIG. 22.

Referring to FIGS. 12–16, membranes fabricated into inflatable bladders by blow molding are shown. To form the bladders, single layer parisons of the polyester-modified polyurethane material are extruded as illustrated in FIGS. 21–23. Thereafter, the parisons are blown and formed using conventional blow molding techniques. The resulting bladders, examples of which are shown in FIGS. 12 and 15, are then inflated with the desired captive gas to the preferred initial inflation pressure and then the inflation port (e.g. inflation port 38) is sealed by RF welding.

Figure 17:
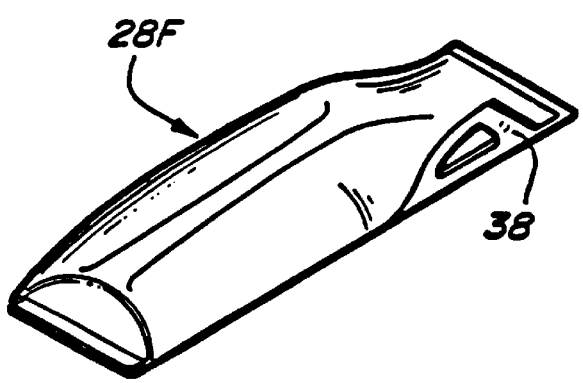
FIG. 17 is a perspective view of a membrane embodiment according to the teachings of the present invention formed into a shoe cushioning device.
Figure 18:
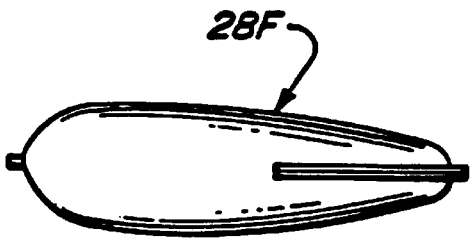
FIG. 18 is a side view of the membrane illustrated in FIG. 17.

Still another embodiment formed from a membrane of the present invention is shown in FIGS. 17 and 18. The air bladder is fabricated by forming extruded single layer tubing having a desired thickness range. The tubing is collapsed to a lay flat configuration and the opposite walls are welded together at selected points and at each end using conventional heat sealing or RF welding techniques. The cushioning device is then inflated through a formed inflation port 38 to the desired inflation pressure which ranges from 5 psi ambient to 100 psi, and preferably from 5 to 50 psi, with a captive gas such as nitrogen.

Figure 25:
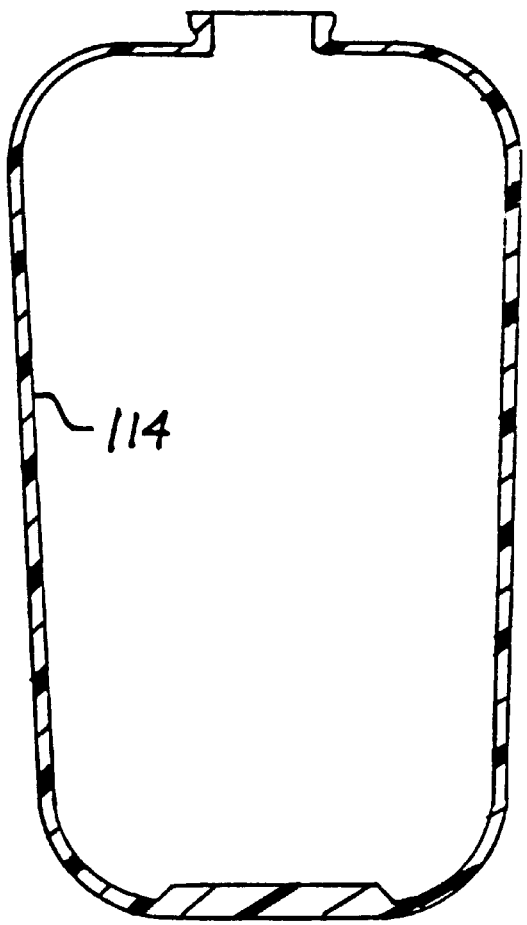
FIG. 25 is a sectional view of a product formed from a monolayer membrane according to the teachings of the present invention.

In addition to employing the membranes of the present invention as cushioning devices or air bladders as described above, still another highly desirable application for the membranes of the present invention is for accumulators as illustrated in FIGS. 19, 20 and 25.

Referring to FIG. 25, there is shown an accumulator embodiment formed from a monolayer membrane as described above. Likewise, referring to FIGS. 19 and 20, there are shown two alternative accumulator embodiments formed from a multi-layer membrane of the present invention. Accumulators, and more particularly, hydraulic accumulators are used for vehicle suspension systems, vehicle brake systems, industrial hydraulic accumulators or for other applications having differential pressures between two potentially dissimilar fluid media. The membrane 124 separates the hydraulic accumulator into two chambers or compartments, one of which contains a gas such as nitrogen and the other one of which contains a liquid. Membrane 124 includes an annular collar 126 and a flexible body portion 128. Annular collar 126 is adapted to be secured circumferentially to the interior surface of the spherical accumulator such that body portion 128 divides the accumulator into two separate chambers. The flexible body portion 128 moves generally diametrically within the spherical accumulator and its position at any given time is dependant upon the pressure of the gas on one side in conjunction with the pressure of the liquid on the opposite side.

By way of further example, FIG. 20 illustrates a product in the form of a hydraulic accumulator including a first layer 114 of the polyester-modified polyurethane barrier material of the invention. The product may be a monolayer of the polyester-modified polyurethane barrier material or may additionally include layers 112 and 116 formed from one or more thermoplastic elastomers. As shown, the first layer 114 only extends along a segment of the entire accumulator body portion. It may be desirable to utilize such embodiments, otherwise referred to herein as "intermittent constructions" under circumstances where the delamination potential of a multilayer embodiment along certain segments of a product is greatest. One such location is along the annular collar 126 of the bladder or diaphragm for hydraulic accumulators in laminate embodiments. Thus, while the laminate membranes of the present invention are generally more resistant to delamination and do a better job of preventing gas from escaping along interfaces between layers such as those occurring along the annular collar via capillary action, it should be recognized that the membranes 110 described herein can include segments which do not include layer 114.

As mentioned, the membranes as disclosed herein can be formed by various processing techniques including but not limited to extrusion, profile extrusion, injection molding, and blow molding and may be sealed to form an inflatable bladder by heat sealing or RF welding of the tubing and sheet extruded film materials.

The membranes, whether in the form of sheet, substantially closed containers, cushioning devices, accumulators or other structures, preferably will have a tensile strength on the order of at least about 2500 psi; a 100% tensile modulus of between about 350–3000 psi and/or an elongation of at least about 250% to about 700%.

Sheet can be made by forcing molten polymer formed in the extruder through a coat hanger die. Collapsed tubing and parisons used in blow molding are made by forcing molten plastic generated by an extruder through an annular die.

The polyester-modified polyurethane barrier material is preferably used as single layer membrane.

An important objective, especially with regard to membranes employed as cushioning devices for footwear, is to provide membranes which are capable of retaining captive gases for extended periods of time. In general, membranes of the polyester-modified polyurethane barrier material which offer gas transmission rate values of 15.0 or less for nitrogen gas as measured according to the procedures designated at ASTM D-1434-82 are acceptable candidates for extended life applications. Thus, while the membranes of the present invention can have varying thicknesses depending mainly on the intended use of the final product, the membranes of the present invention will preferably have a gas transmission rate value of 15.0 or less, regardless of the thickness of the membrane. Likewise, while nitrogen gas is the preferred captive gas for many embodiments and serves as a benchmark for analyzing gas transmission rates in accordance with ASTM D-1434-82, the membranes can contain a variety of different gases and/or liquids.

In preferred embodiments, the membranes of the present invention will have a gas transmission rate of 10.0 and still, more preferably, will have gas transmission rates of 7.5 or less for nitrogen gas. Still more preferably, the membranes of the present invention will have a gas transmission rate of 5.0 or less and, still more preferably yet, will have a gas transmission rate of 2.5 or less for nitrogen gas. Under the most highly preferred embodiments, the membranes of the present invention will have a gas transmission rate of 2.0 or less for nitrogen gas.

In addition to the improved resistance to gas transmission offered by the various products formed from the polyester diol based polyurnthanes described herein, products made from polyester diol based polyurethanes have also shown a marked improvement in durability over thermoplastic polyurethanes which do not include polyester polyols.

Upon inflating the cushioning devices to 20.0 psig with nitrogen gas, each sample was intermittently compressed by a reciprocating piston having a 4.0 inch diameter platen. The stroke of each piston was calibrated to travel a height which would compress each sample to an average of 25.0% of the initial inflated height at maximum stroke. The reciprocating pistons were then allowed to cycle or stroke until a part failure was detected. Part failure, as the term is used herein, is defined as a sufficient leakage of the nitrogen gas and deflation of the cushioning device to cause a lever placed in identical locations along each of the cushioning devices to contact a microswitch which stops the reciprocating piston stroke. The total number of cycles or strokes were then recorded for each sample with a high number of strokes being indicative of a more durable material. Preferably, permanently inflated cushioning devices should be capable of withstanding at least about 200,000 cycles to be considered for applications as footwear components.

In addition to a high degree of durability, it is often desirable to form products which are relatively transparent in nature, i.e. products which meet certain standards in terms of the yellowness level detected and the transmission of light through the material. For example, transparency of the product is often a consideration for cushioning devices such as those utilized as components of footwear wherein the cushioning device is visually accessible. Cushioning devices formed from the polyester-modified polyurethane barrier material of the invention have proven to be useful for shoe components since the material has been shown to offer acceptable levels both in terms of the yellowness level detected and the light transmission through the material.

While the bladders of the invention have been described for the highly useful applications of cushioning devices for footwear and for accumulators, it should be appreciated that the membranes of the present invention have a broad range of applications, including but not limited to bladders for inflatable objects such as footballs, basketballs, soccer balls, inner tubes; flexible floatation devices such as tubes or rafts; as a component of medical equipment such as catheter balloons; as part of an article of furniture such as chairs and seats, as part of a bicycle or saddle, as part of protective equipment including shin guards and helmets; as a supporting element for articles of furniture and, more particularly, lumbar supports; as part of a prosthetic or orthopedic device; as a portion of a vehicle tire, particularly the outer layer of the tire; and as part of certain recreation equipment such as components of wheels for in-line or roller skates.

The invention is further described in the following examples. The examples are merely illustrative and does not in any way limit the scope of the invention as described and claimed. All parts are parts by weight unless otherwise noted.

To prepare Samples 1–12 as set forth in Table I for gas transmission rate analysis, the polyester polyol-modified urethane was initially prepared by adding one or more of the following constituents to a 2000 ml reaction flask: (1) polyester polyol; (2) difunctional extender; and (3) processing aids such as waxes and antioxidants. Thereafter, this hydroxyl component was heated to between approximately 95° C.–115° C. (depending on the composition) and stirred to dissolve and homogenize the constituents. Subsequently, a vacuum of less than 0.2 mm Hg was applied under constant stirring to control foaming. After foaming was completed, the flask was degassed for approximately 30 minutes until virtually all bubbling ceased.

Next, the isocyanate component was prepared by disposing a diisocyanate in a 250 ml polypropylene beaker and placing the diisocyanate in an oven heated to between approximately 50–65° C. Upon obtaining a temperature of between about 50–65° C., the desired amount of the isocyanate constituent was weighted out and the catalyst, if any, was added to the isocyanate constituent under constant mixing.

Once the catalyst was fully mixed in, the desired amount of hydroxyl component was added to the isocyanate component to effectuate polymerization. As polymerization began and the viscosity increased (generally between about 7–12 seconds after addition), the reaction product was poured into pans coated with a desirable release agent and allowed to fully cool. Upon cooling, the newly formed polymer was cut into granules and dried for approximately 2–4 hours at between 85–100° C. Thereafter, Samples 1–10, as set forth in Table I, were prepared by compression molding granules of plastic into sheets to conduct analysis relating to gas transmission properties.

With regard to Sample 11 as illustrated in Table I, after forming the polyester polyol based urethane as described above, 70.0 wt. % of the material was blended and extruded along with the 30.0 wt. % BAREX™ 210 available from BP Chemical, Inc., at a temperature of approximately 420° F. to provide a blended sample for gas transmission analysis. Further, with regard to Sample 12, a membrane was formed for gas transmission analysis by blending 70.0 wt. % of the polyester polyol based urethane set forth in Sample 12 with 30.0 wt. % of the BAREX™ 210 at a temperature of approximately 420° F.

TABLE I*

| | Gas Transmission Rates For Single Layers | | | | | | | | | | | | | |
| --- | --- | --- | --- | --- | --- | --- | --- | --- | --- | --- | --- | --- | --- | --- |
| Formulation | 1 | 2 | 3 | 4 | 5 | 6 | 7 | 8 | 9 | 10 | 11 | 12 | 13 | 14 |
| Polybutanediol Adipate | | | | | | | | | | | | | | |
| (a) 2000 m.w.[1] | 43.12 | | | | | | | | | | | | | |
| (b) 700 m.w.[2] | 15.09 | | | | | | | | | | | | | |
| Ethylene Glycol Adipate | | | | | | | | | | | | | | |
| (a) 1000 m.w.[3] | | 61.11 | 62.29 | 49.18 | 60.63 | 49.60 | 30.26 | 16.39 | | 42.84 | 51.23 | | | |
| (b) 500 m.w.[4] | | | | | | | 22.69 | 32.77 | | | | | | |
| HD Adipate/ HD Isophthalate | | | | | | | | | | | | | | |
| (a) 1000 m.w.[5] | | | | | | | | | | | 18.36 | | | |
| Ethylene Glycol Glutarate | | | | | | | | | | | | | | |
| (a) 1000 m.w.[6] | | | | | | | | | 51.23 | | | | | |
| Ethylene Glycol | | | 4.25 | | | | | | | | | | | |
| Dipropylene glycol | 0.58 | | | | | | | | | | | | | |
| Butyl Carbitol | 0.21 | | | | | | | | 0.25 | | 0.25 | | | |
| 1,4 Butanediol | 7.37 | 6.05 | | 9.96 | 6.00 | 8.93 | 6.81 | 7.37 | 9.22 | 6.06 | 9.22 | | | |

TABLE I*-continued

Gas Transmission Rates For Single Layers

| Formulation | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| H12MDI[7] | | | | | | 41.07 | 39.84 | | | | | | | |
| MDI[8] | 33.04 | 32.5 | | 40.52 | | | | 43.15 | 38.96 | 32.40 | 38.96 | | | |
| MDI/liq. MDI[9] | | | 33.12 | | 33.03 | | | | | | | | | |
| Irganaox 1010[10] | 0.125 | 0.15 | 0.15 | 0.15 | 0.15 | 0.15 | 0.15 | 0.15 | 0.15 | 0.15 | 0.15 | | | |
| Advawax 280[11] | 0.125 | 0.15 | 0.15 | 0.15 | 0.15 | 0.15 | 0.15 | 0.15 | | 0.15 | | | | |
| Wax[12] | 0.30 | | | | | | | | 0.15 | | | | | |
| Catalyst[13] | 0.04 | 0.04 | 0.04 | 0.04 | 0.04 | 0.10 | 0.10 | 0.02 | 0.04 | 0.04 | 0.04 | | | |
| Kemamide W-40[14] | | | | | | | | | | | 0.15 | | | |
| Pellethane 2355-85 ATP[15] | | | | | | | | | | | | 100.0 | 100.0 | |
| Pellethane 2355-95 AE[16] | | | | | | | | | | | | | | 100.0 |
| Total Wt. % | 100.0 | 100.0 | 100.0 | 100.0 | 100.0 | 100.0 | 100.0 | 100.0 | 100.0 | 100.0 | 100.0 | 100.0 | 100.0 | 100.0 |

*All values provided in Table I are in weight percents (wt. %)

A. FOMREZ™ 44-56 available from Witco Chemical
2. FOMREZ™ 44-160 available from Witco Chemical
3. FOMREZ™ 22-112 available from Witco Chemical
4. FOMREZ™ 22-225 available from Witco Chemical
5. FOMREZ™ 8066-120- 50 parts 1,6 hexanediol adipate and 50 parts HD lsophthalate polyester polyol available from Witco Chemical
6. UrethHall™ 2050 available from C.P. Hall Company
7. DESMODUR W available from BAYER AG (America)
8. ISONATE™ 2125M available from Dow Chemical Co.
9. Blend of 80 parts ISONATE™ 2125 and 20 parts ISONATE™ 2143 available from Dow Chemical Co.
10. IRGANOX™ 1010 available from Ciba-Gigy Chemical Co.
11. ADVAWAX™ 280 available from Morton Plastics, Inc.
12. Montan ester wax
13. Blend of 50 parts stannous octoate and 50 parts dioctyl phthalate
14. Kemamide W-40 (ethylene bis-stearamide wax) available from Witco Chemical
15. PELLETHANE™ 2355-85 ATP available from Dow Chemical Co.
16. PELLETHANE™ 2355-95 AE available from Dow Chemical Co.

TABLE II

| Sample Number | Average Thickness | GTR (cc/m$^2$ * atm * day) | GTR (cc/m$^2$ * atm * day) Normalized to 20 mils thickness |
|---|---|---|---|
| 1 | 16.25 mils | 30.95 | 25.15 |
| 2 | 15.2 mils | 11.71 | 8.9 |
| 3 | 17.13 mils | 9.13 | 7.82 |
| 4 | 18.49 mils | 6.58 | 6.08 |
| 5 | 17.54 mils | 7.07 | 6.19 |
| 6 | 19.93 mils | 9.22 | 9.19 |
| 7 | 19.93 mils | 6.19 | 6.17 |
| 8 | 18.31 mils | 1.20 | 1.10 |
| 9 | 16.93 mils | 3.47 | 2.93 |
| 10 | 14.47 mils | 17.92 | 12.96 |
| 11 | 19.22 mils | 1.24 | 1.19 |
| 12 | 17.1 mils | 2.73 | 2.33 |
| 13 | 19.95 mils | 36.42 | 36.33 |
| 14 | 18.25 mils | 24.12 | 22.01 |

As illustrated in Table II, each of the Samples 2–12 demonstrated better gas transmission rate results than the control Samples 13–14, which were formed of commercially available thermoplastic urethane resins. Each of the samples, namelyn Samples 2–10 which relate to polyethylene glycol adipate and ethylene glycol glutarate based urethanes and Samples 11–12 which relate to polyethylene glycol adipate based urethane blends, including BAREX™ 210, generally demonstrated better gas transmission rate values than the polybutanediol adipate bases urethane of Sample 1. As illustrated, each of the Samples 2–12, exhibited a gas transmission rate of less than 15.0 for $N_2$ at 20 mils.

A multi-layer sample was also prepared by laminating two layers of the polyester polyol based urethane as set forth in Sample 11 of Table I along with a third layer of commercially available material known as ISOPLAST™. To laminate the multi-layer sample, a sheet of 5 mil ISOPLAST™ film was sandwiched between two layers of the polyester polyol based urethane, each having a thickness of 19 mils. The multi-layer sample was then pressed within a hydraulic press having upper and lower platens heated to about 420° F. The films were pressed together at a pressure of about 2,000 psig to give rise to a sample having an overall thickness of approximately 18.25 mils.

Upon conducting the gas transmission rate analysis on the multi-layer sample, it was discovered that the sample had a GTR of 8.87 for nitrogen at 18.25 mils and as normalized to 20.0 mils had a GTR of 8.09. Thus, the multi-layer sample also met the objective of a gas transmission rate of less than 15.0.

Finally, in addition to the monolayer and multi-layer membrane samples as set forth above, a thermoset version of a polyester polyol based urethane was also prepared and analyzed for gas transmission.

The sample, as set forth in Table III below, was prepared by dehydrating and degassing the polyester polyol under a vacuum for two hours at 100° C. and cooled to 60° C. at which time the catalyst was added. Concurrently, the Isonate™ 2143L was heated to 45° C. and degassed for twenty minutes before its addition to the polyester component. The polyester polyol and polyisocyanate were then mixed and stirred carefully in a polypropylene beaker to avoid the introduction of air. Upon mixing, the mixture was cast into a warm plaque mold where it was allowed to cure for two hours at ambient temperature and pressure before demolding. The resulting membrane was allowed to remain at ambient conditions for seven days prior to testing.

TABLE III

| Ethylene glycol adipate (a) 1000 m.w.[1] | 77.36 |
|---|---|
| MDI[2] | 22.34 |
| Catalyst[3] | 0.30 |
| | 100.0 |

[1]FOMREZ ™ 22-225 available from Witco Chemical
[2]ISONATE ™ 2143L which is a liquid MDI available from Dow Chemical Co. of Midland, MI.
[3]COCURE ™ 55 which is available from Caschem Inc., of Bayonne, N.J.

The thermoset version of the polyester polyol based urethanes as set forth in Table III exhibited a gas transmission rate of 3.07 for a 73 mils thickness. Upon normalizing, the gas transmission rate was calculated to be 11.2 for $N_2$ based on a 20 mil thickness. Thus, both thermoplastic and thermoset materials appear to be useful in accordance with the teachings of the present invention.

For example, as illustrated in Table IV below, multiple samples were prepared and analyzed for durability utilizing a test method known as as a KIM test. In accordance with the KIM test procedures, two sheets were extruded from differing materials with each sheet being formed into identically shaped cushioning device components having an average wall thickness of 18 mils. The material utilized for the Set A cushioning devices is the same as that set forth in Table I as Formulation No. 11. The Set B cushioning devices were made from a material such as Pellethane 2355-85A, a thermoplastic urethane that does not contain any polyethylene glycol adipate soft segments.

Upon inflating the cushioning devices to 20.0 psig with nitrogen gas, each sample was intermittently compressed by a reciprocating piston having a 4.0 inch diameter platen. The stroke of each piston was calibrated to travel a height which would compress each sample to an average of 25.0% of the initial inflated height at maximum stroke. The reciprocating pistons were then allowed to cycle or stroke until a part failure was detected. Part failure, as the term is used herein, is defined as a sufficient leakage of the nitrogen gas and deflation of the cushioning device to cause a lever placed in identical locations along each of the cushioning devices to contact a microswitch which stops the reciprocating piston stroke. The total number of cycles or strokes were then recorded for each sample with a high number of strokes being indicative of a more durable material. Preferably, permanently inflated cushioning devices should be capable of withstanding at least about 200,000 cycles to be considered for applications as footwear components.

As can be seen from a review of Table IV, the cushioning devices of Set A formed from the polyester polyol based urethane outperformed the cushioning devices formed from the aromatic thermoplastic based urethane of Set B by over three times as many cycles. Thus, the polyester polyol based urethanes utilized under the present invention not only offer better resistance to undesired gas transmission, but also have been shown to offer enhanced durability over thermoplastic urethanes which do not include polyester polyol soft segments having eight or less carbon atoms having eight or less carbon atoms in the repeating units.

TABLE IV

| Sample No. | Avg No. of Cycles |
|---|---|
| Set A* | 754,111 |
| Set B** | 217,797 |

*Average of 9 tests
**Average of 10 tests

In addition to a high degree of durability, it is often desirable to form products which are relatively transparent in nature, i.e. products which meet certain standards in terms of the yellowness level detected and the transmission of light through the material. For example, transparency of the product is often a consideration for cushioning devices such as those utilized as components of footwear wherein the cushioning device is visually accessible.

Cushioning devices formed from Pellethane 2355-87 ATP, an aromatic thermoplastic based urethane, have proven to be useful for shoe components since the material has been shown to offer acceptable levels both in terms of the yellowness level detected and the light transmission through the material. Thus, polyester polyol-modified polyurethanes would preferably have similar and, more preferably, improved transparency characteristics as compared to aromatic thermoplastic urethanes such as Pellethane 2355-87ATP, among others.

Samples of both Pellethane 2355-87ATP and a polyester polyol based urethane including: 50.96 wt. % FOMREZ 22-122 (1000 m.w.); 9.11 wt. % 1,4 Butanediol; 38.81 wt. % ISONATE 2125M; 0.50 wt. % IRGANOX 1010; 0.15 wt. % ADVAWAX 280; 0.30 wt. % montan ester wax; and 0.02 wt. % catalyst, were prepared by extruding smooth sided, collapsed tubes having an average wall thickness of 32 mils. Each sample was thereafter analyzed for its yellowness index and the total transmission of light therethrough utilizing a Hunter Lab Color QUEST™ Spectocolorimeter in accordance with the instrument's instruction manual.

The yellowness index readings were standardized in the {rsin} mode, and readings were taken along the reflectance port. The total transmission measurements were also standardized and the measurements were taken by readings without glass slides along the transmission ports.

The Pellethane 2355-87ATP had a yellowness index of 4.00 and a total transmission of light of 90.85% based on a maximum value of 100.0% transmission. The polyester polyol-modified polyurethane had a yellowness index of 1.52 and a total transmission of light of 91.75%. The polyester polyol-modified polyurethanes, thus, not only appear to be more durable than aromatic thermoplastic based urethanes but also appear to offer better values both in terms of a lower yellowness index and a higher light transmission. This improvement in terms of both decreased yellowness and an increased transmission of light should enhance the aesthetic characteristics of many final products.

The invention has been described in detail with reference to preferred embodiments thereof. It should be understood, however, that variations and modifications can be made within the spirit and scope of the invention and of the following claims.

What is claimed is:

1. A durable membrane comprising at least one layer having a polymeric gas barrier component consisting essentially of a thermoplastic polyester polyol-modified polyurethane, said membrane having a gas transmission rate of 15.0 or less for nitrogen gas, wherein said polyester polyol has repeating units in which the total number of carbon atoms is about eight or less; and said membrane being a free-standing, flexible film.

2. A membrane according to claim 1, wherein said polyester polyol of is selected from the group consisting of the reaction product of (a) at least one member selected from the group consisting of dicarboxylic acids having from about two to about six carbon atoms, anhydrides thereof, and combinations thereof; and (b) at least one diol having six or less carbon atoms.

3. A membrane according to claim 2, wherein the component (a) is selected from the group consisting of adipic, glutaric, succinic, malonic and oxalic acids, anhydrides thereof, and combinations thereof.

4. A membrane according to claim 3, wherein the component (a) includes adipic acid.

5. A membrane according to claim 2, wherein component (b) includes at least one member selected from the group consisting of ethylene glycol, propanediol, butanediol, neopentyl glycol, pentanediol, hexanediol, and combinations thereof.

6. A membrane according to claim 2, wherein the component (b) includes ethylene glycol.

7. A membrane according to claim 2, wherein said polyurethane further comprises at least one extender.

8. A membrane according to claim 7, wherein said extender is selected from the group consisting of ethylene glycol, 1,3 propylene glycol, 1,4-butanediol, 1,6-hexanediol, and combinations thereof.

9. A membrane according to claim 7, wherein the ratio of polyester polyol to extender is from about 1:1 to about 1:8.

10. A membrane according to claim 7, wherein the polyurethane is formed with a ratio of equivalents of isocyanate of from about 0.95 to about 1.10 per equivalent of combined polyester polyol and extender equivalents.

11. A membrane according to claim 1, further comprising a hydrolytic stabilizer.

12. A membrane according to claim 11, wherein said hydrolytic stabilizer is selected from the group consisting of carbodiimides, polycarbodiimide and epoxidized soy bean oil.

13. A membrane according to claim 1, wherein said membrane has a gas transmission rate of less than about 10.0 for nitrogen gas.

14. A membrane according to claim 1, wherein said membrane has an elongation of at least about 250%.

15. The membrane according to claim 1, wherein said membrane has a elongation of from about 250% to about 700%.

16. A membrane according to claim 1, wherein said membrane has a tensile strength of at least about 2,500 psi.

17. A membrane according to claim 1, wherein said membrane has an 100% tensile modulus of between 350 to about 3,000 psi.

18. A bladder comprising a membrane, wherein said membrane comprises as a gas-barrier component a polyester polyol-modified polyurethane, said membrane having a gas transmission rate of 15.0 or less for nitrogen gas wherein said polyester polyol has repeating units in which the total number of carbon atoms is about eight or less.

19. A bladder according to claim 18, wherein said bladder has an internal pressure of from about 5 psi to about 35 psi.

20. A bladder according to claim 18, wherein the polymeric component of said membrane consists essentially of said polyester polyol-modified polyurethane.

* * * * *